United States Patent [19]

Sun et al.

[11] Patent Number: 4,986,671
[45] Date of Patent: Jan. 22, 1991

[54] THREE-PARAMETER OPTICAL FIBER SENSOR AND SYSTEM

[75] Inventors: Mei H. Sun, Los Altos; Kenneth A. Wickersheim, Menlo Park, both of Calif.

[73] Assignee: Luxtron Corporation, Mountain View, Calif.

[21] Appl. No.: 336,836

[22] Filed: Apr. 12, 1989

[51] Int. Cl.$^5$ .................... G01K 11/20; G01K 17/00; G01D 5/34; G01L 9/00

[52] U.S. Cl. ................................ 374/131; 374/143; 374/161; 374/29; 374/43; 350/96.15; 250/368; 250/227.14; 73/705; 73/204.23; 128/666; 128/667; 128/692; 128/675; 128/736

[58] Field of Search .................. 374/29, 30, 131, 143, 374/159, 161, 162, 142, 43, 44, 54, 45, 130, 141; 356/44, 43; 350/96.15; 250/227, 368; 128/665, 666, 667, 692, 675, 673, 736, 634; 73/705, 204.23

[56] References Cited

U.S. PATENT DOCUMENTS

| | | |
|---|---|---|
| 3,249,105 | 5/1966 | Polanyi . |
| 4,016,761 | 4/1977 | Rozzell et al. .................. 374/161 |
| 4,075,493 | 2/1978 | Wickersheim .................. 374/159 |
| 4,136,566 | 1/1979 | Christensen . |
| 4,140,393 | 2/1979 | Cetas .................................. 356/43 |
| 4,158,310 | 6/1979 | Ho ..................................... 73/705 |
| 4,179,927 | 12/1979 | Saaski ............................... 374/152 |
| 4,245,507 | 1/1981 | Samulski ........................... 374/159 |
| 4,487,206 | 12/1984 | Aagard . |
| 4,509,370 | 4/1985 | Hirschfeld . |
| 4,521,683 | 6/1985 | Miller ............................... 250/221 |
| 4,545,253 | 10/1985 | Avicola ............................. 250/227 |
| 4,547,668 | 10/1985 | Tsikos .............................. 250/227 |
| 4,569,570 | 2/1986 | Brogårdh et al. ............... 250/486.1 |
| 4,581,528 | 4/1986 | Brogårdh et al. ............... 250/227 |
| 4,581,530 | 4/1986 | Brogårdh et al. ............... 250/227 |
| 4,588,886 | 5/1986 | Snider . |
| 4,593,701 | 6/1986 | Kobayashi et al. .............. 128/634 |
| 4,599,901 | 7/1986 | Hirschfeld . |
| 4,599,908 | 7/1986 | Sheridan et al. ................. 250/227 |
| 4,600,836 | 7/1986 | Berthold, III et al. . |
| 4,611,600 | 9/1986 | Cohen . |
| 4,621,929 | 11/1986 | Phillips ............................. 374/131 |
| 4,652,143 | 3/1987 | Wickersheim et al. ......... 374/131 |
| 4,672,199 | 6/1987 | Anderson et al. . |
| 4,687,927 | 8/1987 | Iwamoto et al. . |
| 4,691,708 | 9/1987 | Kane . |
| 4,711,246 | 12/1987 | Alderson . |
| 4,752,141 | 6/1988 | Sun et al. ......................... 374/131 |
| 4,814,562 | 3/1989 | Langston ........................... 250/227 |

OTHER PUBLICATIONS

Mathvssek et al., "Fabrication and Investigation of Drawn Fiber Tapers with Spherical Microlenses", Journal of Optical Communications, vol. 5, No. 4, 1985, pp. 142-146.

(List continued on next page.)

Primary Examiner—William A. Cuchlinski, Jr.
Assistant Examiner—Diego F. F. Gutierrez
Attorney, Agent, or Firm—Majestic, Parsons, Siebert & Hsue

[57] ABSTRACT

A single sensor is provided as part of a fiberoptic probe to measure up to three parameters, namely pressure (or force or displacement), temperature, and heat flow or fluid velocity. A solid elastomeric optical element is formed at the end of optical fiber transmission medium, and adjacent light reflective and temperature dependent materials are formed on the resulting convex surface of the optical element. The amount of light reflected is proportional to the force or pressure against the element. The temperature dependent material is preferably a luminescent material. Over the luminescent material is formed a layer of material that is absorptive of infrared radiation, thereby allowing a determination of characteristics of heat or fluid flow by measuring the rate at which heat is carried away from the infrared heated layer. The sensor can be formed at the end of a single optical fiber, thereby having extensive applications where a very small sensor is required. One such application is a medical or clinical one, where the sensor is mounted in a catheter for providing pressure, flow and temperature of the blood in a blood vessel.

44 Claims, 3 Drawing Sheets

OTHER PUBLICATIONS

Sun et al., "Advances in Fluoroptic Thermometry: New Applications in Temperature Measurement", presented at Digitech '85 of the Instrument Society of America, May 14–16, 1985.

Wickersheim and Sun, "Improved Surface Temperature Measurement Using Phosphor-Based Fiberoptic Techniques", *Research and Development*, Nov. 1985.

Sun et al., "Improved Surface Temperature Measurement Techniques for Use in Conjunction with Electronics Processing and Testing", presented at the Semi-Conductor, Thermal and Temperature Measuring Symposium, Dec. 10, 1986.

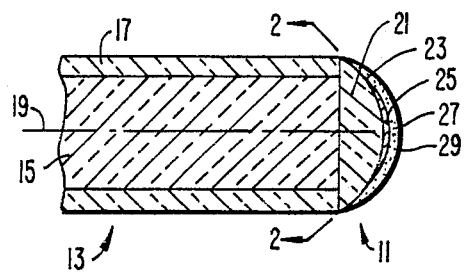
FIG._1.
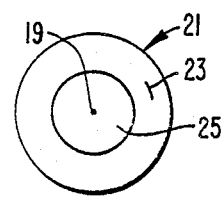
FIG._2.
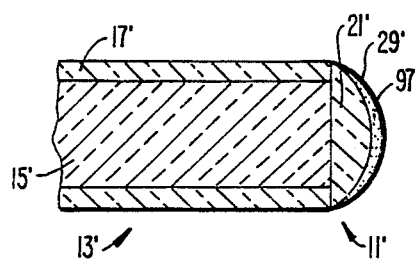
FIG._3.
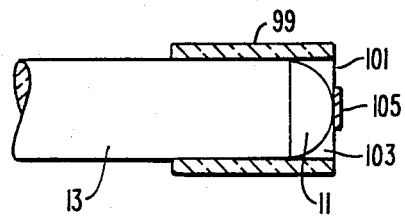
FIG._4.
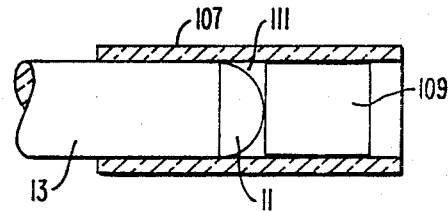
FIG._5.

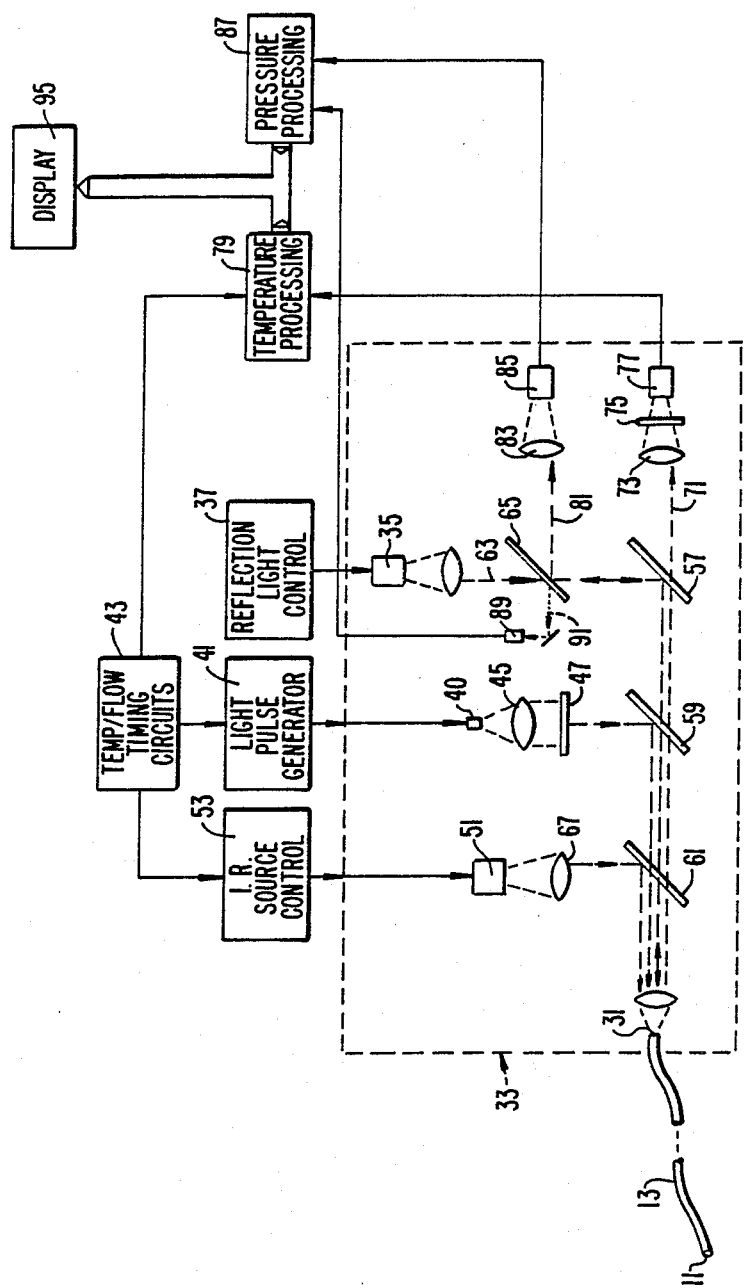
FIG.__6.

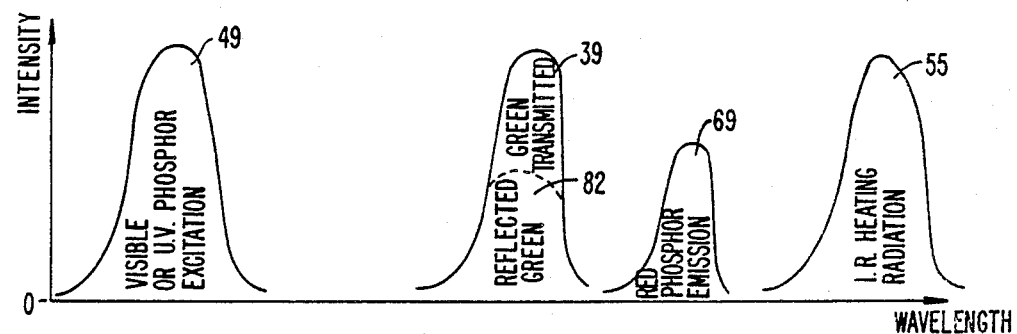
FIG._7.

THREE-PARAMETER OPTICAL FIBER SENSOR AND SYSTEM

BACKGROUND OF THE INVENTION

This invention relates generally to techniques and systems for measuring one or more parameters with optical fiber sensors.

During the mid to late 1970's, many suggestions and development efforts were directed toward measuring various parameters with a specially designed optical sensor provided at an end of a length of optical fiber, the other end of which is connected to a measuring electro-optical instrument. Much of this work was motivated by the desire to provide a non-metallic sensor that could be used in the presence of electromagnetic fields without either the measurement being affected by the fields or the sensor itself perturbing the fields.

U.S. Pat. No. 4,016,761 - Rozzell et al. (1977) describes the use of liquid crystal material as a temperature sensor, such a material having a varying absorptive characteristic as a function of temperature. U.S. Pat. No. 4,140,393 - Cetas (1979) proposes the use of birefringement material as a temperature probe. U.S. Pat. No. 4,136,566 - Christensen (1979) suggests the use of the temperature dependent light absorption characteristics of gallium arsenide for a temperature sensor. U.S. Pat. No. 4,179,927 - Saaski (1979) proposes a gaseous material having a temperature dependent light absorption.

U.S. Pat. No. 4,075,493 - Wickersheim (1978) suggests the use of a luminescent material as a temperature sensor, exciting radiation of one wavelength range being passed along the optical fiber from the measuring instrument, and temperature dependent luminescent radiation being emitted from the sensor back along the communicating optical fiber for detection and measurement by the instrument. It is the luminescent sensor technology which has found the greatest commercial applicability in fiber optic measurements, primarily for reasons of stability, wide temperature range, ability to minimize the effect of non-temperature light variations, small sensor size and the like. An example of a current commercial technology is given in U.S. Pat. No. 4,652,143 - Wickersheim et al. (1987).

Optical fiber temperature measurement techniques have been pursued for use primarily in applications where traditional electrical temperature sensors, such as thermistors and thermocouples, do not function well. One such application is in a strong radio frequency or microwave field, as previously mentioned. An example of this is a measurement of the temperature of an object being heated by a microwave field in an industrial heating, drying or curing application. Another example is the measurement of temperature of a human by implanting a sensor within an area of the body being heated by microwave energy, such as is used in the cancer treating hyperthermia techniques.

As the fiber optic temperature measurement technology has become commercially accepted, there has been a growing demand for similar devices that measure additional parameters, such as flow, pressure, index of refraction, or humidity. An example of a luminescent fiberoptic probe that can be used to measure the velocity of fluid flow, among other related parameters, is given in U.S. Pat. No. 4,621,929 - Phillips (1986). Infrared radiation is directed to the sensor along the optical fiber and is absorbed by a layer of material provided for that purpose. Once heated, the sensor is then allowed to be cooled by a flow of fluid, such cooling being measured by the luminescent sensor. The rate of cooling is proportional to the heat transfer characteristics and flow of the surrounding liquid.

U.S. Pat. No. 4,752,141 - Sun et al. (1988) describes a luminescent sensor for simultaneously measuring pressure and temperature. An elastomeric optical element is attached to an end of an optical fiber with luminescent material being coated on an outer convex surface of the optical element. Force supplied to compress the optical element deforms the luminescent coated surface and thus affects the luminescent optical signal in a way that can be used to detect the magnitude of such force independent of, and simultaneously with, temperature.

It is a primary object of the present invention to provide improvements in both single parameter and multi-parameter optical sensing technology.

It is also an object of the present invention to provide optical fiber sensors that are particularly useful in medical applications. In this connection, it is an object of the present invention to measure several useful parameters with a single sensor having as small a dimension as possible.

SUMMARY OF THE INVENTION

These and additional objects are accomplished by the various aspects of the present invention, wherein, briefly and generally, up to three different parameters may be measured by use of single sensor that can be constructed on the end of a single optical fiber. The three parameters are temperature, pressure and flow. The ability to measure these three parameters in such a small sensor has great applicability in medical applications, such as use in a catheter where space is very limited.

According to one specific aspect of the present invention, pressure (or one of its related parameters, force or displacement) is measured by reflecting light from a surface in the sensor whose curvature changes in response to a change in pressure being experienced by the sensor. In a preferred form, an optical element formed from an elastomeric material is attached to an end of an optical fiber and has an non-planar outer surface thereof that is at least partially covered with a reflecting material.

According to another specific aspect of the present invention, a simultaneous temperature measuring capability is provided by either forming a temperature dependent optical element on the deformable surface around and adjacent to the reflecting material, or, in the case where that temperature dependent element is luminescent material, that material itself may be made to be reflective. In either case, it is preferred that radiation in different wavelength bands be directed against the sensor, one for each of the parameters being measured. This provides easily separable optical signals for each of the parameters being measured.

According to a third aspect of the present invention, a third parameter such as heat flow or fluid velocity is measured by coating the optical temperature measuring element with material that readily absorbs infrared radiation. After the sensor is heated by infrared radiation being passed through the communicating optical fiber, the characteristics of its cooling from the surrounding fluid flow is measured with the optical temperature sensor.

In a preferred form of this three-parameter sensor, the deformable, non-planar surface of the sensor optical element is provided with three layers, one on top of each other, one layer for each of the parameters being measured. In this form, interrogating light radiation is directed from the instrument to the sensor in a different wavelength band for each such parameter.

Additional objects, advantages and features of the present invention will become apparent from the following description of its preferred embodiments, which description should be taken in conjunction with the accompanying drawings.

BRIEF DESCRIPTION OF THE DRAWINGS

FIG. 1 is a sectional view of one embodiment of sensor according to the present invention;

FIG. 2 is an end view of the sensor of FIG. 1, with portions removed, taken along a curved surface indicated by the section 2—2 thereof;

FIG. 3 shows a sectional view of a sensor according to another embodiment of the present invention;

FIG. 4 shows one variation of either of the sensor embodiments of FIGS. 1 or 3;

FIG. 5 shows another variation of either of the embodiments of FIGS. 1 or 3;

FIG. 6 is a schematic diagram of an electro-optical instrument with which any of the embodiments and variations thereof illustrated in FIGS. 1-5 can be used; and FIG. 7 shows the wavelength bands occupied by various of the optical signals in the system of FIG. 6.

DESCRIPTION OF THE PREFERRED EMBODIMENTS

FIG. 1 is a sectional view of an optical fiber sensor according to one embodiment of the present invention. A sensor 11 is attached to an end of an optical fiber 13. The optical fiber 13 is of a readily commercially available type, having a core 15 that is surrounded by a cladding 17. A usual outer protective jacket is not illustrated in these drawings. A central axis 19 of the optical fiber 13 is indicated for discussion purposes. The sensor 11 is attached directly to the core 15 at the fiber end.

The sensor 11 includes an optical element 21 as a principal component. The element 21 is made from a compressible, elastomeric material and is formed into an approximately hemispherical shape, resulting in a convex outer surface 23. On that surface are provided three additional layers, one for each of the parameters that the sensor of FIG. 1 is designed to measure. A reflective coating 25 is applied directly to the convex surface 23. The reflective layer 25 is used to measure pressure or the related quantities of force or displacement. A layer 27 of a temperature dependent optical sensing material is coated over the reflective layer 25 and any remaining exposed portions of the surface 23 of the element 21. The layer 27 is used to measure temperature. Finally, a layer 29 of infrared absorbing material is coated over the temperature sensing layer 25, and is used in conjunction with measurement of flow and the like.

The optical element 21 is preferably made to be substantially optically clear and have a refractive index that is substantially the same as that of the optical fiber core 15. The element 21 is made of an elastomeric material that is deformed when force is applied to opposite sides thereof. Such a force, in the course of deforming the elastomeric element 21, changes the curvature of its outer surface 23, and thus affects the level of optical coupling between the reflective layer 25 and the optical fiber 13. This variable coupling, as a function of the force or pressure applied to the sensor 11, provides a detectable variation in the proportion of incident light in the fiber 13 that is returned by the element 25 back along the fiber 13.

Material used for the element 21 should have a memory. That is, the material should return to its original, uncompressed shape shown in FIG. 1 when force against it is removed. The elasticity and compression strength is chosen for the element 21 to be consistent with the range of forces or pressures to be measured.

A silicone elastomer manufactured and sold by Dow Corning under their number 96-083 is a satisfactory material for use in forming the element 21. In order to form the element 21 on the end of the optical fiber 13, the elastomeric material is first spread in a liquid state on a glass plate in a layer that approximates the maximum thickness of the element 21. The free end of the fiber 13 is then brought into contact with the elastomeric material layer. Since the material has good properties of adhesion to the fiber core and cladding, a portion of the elastomeric material layer attaches itself to the end of the fiber 13. When the fiber end is pulled back from the liquid layer, the convexly shaped element 21, as shown in FIG. 1, is the result. The elastomer is then cured by placing it in a heated oven.

The reflective layer 25 is preferably a non-metallic white coating. Since a significant advantage of optical fiber measuring techniques is that the sensors can be used in high level electromagnetic fields without themselves being heated and without perturbing the field, it is undesirable to add any metallic or magnetic material to the sensor.

It will be noted from FIG. 2 that the reflective coating 25 is made circular in shape to have a center approximately coincident with the axis 19 of the optical fiber 13 and it only covers a portion of the exposed convex surface 23 of the optical element 21. In the specific embodiment of FIG. 1, the optical temperature sensing layer 27 is allowed to communicate through that portion of the surface 23 which is around the opaque reflective coating 25. But even in a useful single-parameter variation of the sensor of FIG. 1, wherein the temperature sensitive optical layer 27 and infrared absorbing layer 29 are not utilized, it is desirable to limit the reflective coating to the portion of the circuit 23 whose deformation is the greatest over the range of expected applied forces. It will be recognized that coating of the surface 23 near its outer edge will form a significant area where the amount of light reflected back into the optical fiber will vary very little as the element 21 is compressed and the shape of the surface 23 is changed.

The temperature sensing material 27 can operably be formed of any of the several materials discussed earlier in this application as having been suggested by others for use in optical temperature measuring probes. However, a luminescent material is preferred. Excitation radiation of one wavelength strikes the layer 27 in its region surrounding the opaque reflective material 25, and the temperature dependent luminescent emissions are communicated back along the fiber at a different wavelength. A preferred luminescent material is that described in aforementioned U.S. Pat. No. 4,652,143, the disclosure of which is expressly incorporated herein by reference. The luminescent material is preferably in the form of particles that are held together by a substantially optically clear binder, the binder preferably being the same material as the optical element 21.

This specific luminescent layer 27 itself absorbs very little infrared radiation. Any infrared radiation passed along the optical fiber 13 passes through it to reach the absorbing layer 29 in the regions around the reflective spot 25. An example of such an infrared absorbing material is a low density carbon filled or black pigmented resin. In measuring flow of a fluid in which the sensor 11 is immersed, the layer 29 is first heated by directing infrared radiation along fiber 13 against the sensor 11. When the infrared radiation is turned off, the temperature decrease of the sensor 11 is monitored by the temperature dependent luminescent layer 27. The manner in which this is accomplished is described more completely in aforementioned U.S. Pat. No. 4,621,929, the disclosure of which is expressly incorporated herein by reference.

A significant advantage of the sensor of FIGS. 1 and 2 is that three parameters can be measured by the single, small sensor. Although a multiple fiber bundle can be utilized, the single fiber 13 is preferred in order to minimize the size of the sensor while still permitting enough optical signal to pass along it. A diameter of the single fiber end, and thus of the sensor also, can easily be made to be less than one millimeter, and even less than one-half millimeter, if necessary. The ability to optically measure three parameters with such a small sensor has particular advantages in medical applications where up to three separate sensors would otherwise have to be utilized to obtain the same measurements.

The sensor of FIGS. 1 and 2 is also advantageously employed even when less than all three parameters are being measured. For example, simultaneous measurement of temperature and pressure may be all that is necessary in certain applications, the same sensor as illustrated in FIGS. 1 and 2 being used for such an application by simply omitting the propagation of heating infrared radiation to the sensor. Similarly, the temperature measurement may also be omitted simply by not providing the optical sensing layer 27 with the excitation or other radiation that it needs in order to provide a temperature optical signal. Of course, the temperature sensing layer 27 can be omitted from sensors where it is known that that quantity is not necessary. But it is unlikely that a sensor without a temperature measuring capability will have much usefulness since temperature is desirable at least for correcting for temperature effects of the pressure measurement made by reflecting light from the coating 25.

Referring to FIGS. 6 and 7, an electro-optical instrument is schematically illustrated for simultaneously measuring all three parameters with the sensor of FIGS. 1 and 2. An end 31 of the optical fiber 13 that is opposite to the end carrying the sensor 11 optically communicates with an optical system 33 of the measuring instrument of FIG. 6. The optical system 33 includes three sources of light in different wavelength bands, one source for each of the parameters being measured. In principle, three light sources could emit any of a wide range of spectral inputs. It is useful, however, that the wavelength of each be sufficiently different to allow easy discrimination. For example, a light-emitting diode 35, being controlled by circuits 37 to operate continuously during a measurement, emits light that it reflected from the coating 25 of the sensor 11. In a specific example, the light is limited to the green region, its bandwidth 39 being illustrated in FIG. 7.

For temperature measurements, a useful luminescent material in the layer 27 of the sensor 11 requires use of a flashlamp 40 that is periodically pulsed by control circuits 41, under control of timing circuits 43. After passing through appropriate optics 45, the broad spectral output of the flashlamp 40 is limited by a filter 47 to a deep blue or ultraviolet spectral range 49 illustrated in FIG. 7.

A third source is a diode laser 51 which emits pulses of energy, in response to control circuits 53, that are within the near infrared region of the spectrum, as indicated by the bandwidth 55 of FIG. 7. This is the source of the energy which is absorbed by the layer 29 of the sensor 11 for heating the sensor prior to the subsequent monitoring of the cooling of the sensor in order to determine heat conduction or flow of the fluid that surrounds the sensor 11.

Light from these three sources travels along the optical fiber 13 from a series of three dichroic mirrors 57, 59 and 61. Each of these dichroic mirrors is optically tuned to reflect the bandwidth of a particular source while allowing radiation of other wavelengths to pass through it. Specifically, the dichroic mirror 57 is designed to reflect green light of the bandwidth 39 while allowing light wavelengths outside that band to pass through it. Thus, the green light from the L.E.D. passes as a beam 63 through a beam splitter 65 and then on to the mirror 57.

The dichroic mirror 59 is optically tuned to reflect the luminescent material excitation wavelength range 49 while allowing longer wavelength radiation to freely pass through it. Mirror 61 is tuned to efficiently reflect infrared radiation within the band 55 while allowing shorter wavelengths to freely pass through it. Thus, the infrared output of the diode laser 51 is directed against the mirror 61 through appropriate optics 67.

Two optical signals returned from the sensor 11 by the optical fiber 13 are of interest. One such signal is the luminescent emission, indicated in FIG. 7 to be within a red bandwidth range 69, which easily passes through each of the three dichroic mirrors as a beam 71. Appropriate optics 73 direct the beam 71 through a band pass optical filter 75 and onto a detector 77. An electrical signal output of the detector 77 is processed by circuit 79 in order to determine the temperature of the luminescent material 27 in the sensor 11.

The second signal of interest returned from the sensor is the reflection of the green light from the reflective spot 25 of the sensor 11. This light follows the same path as the green source light 63, until it reaches the beam splitter 65 after having been reflected by the dichroic mirror 57. The beam splitter 65 is selected to transmit about one-half of the incident light against it, thereby reflecting the other half. Thus, about one-half of the intensity of the green light reflected by the sensor 11 is reflected off the beam splitter 65 as a pressure optical signal 81. A spectral component of that signal is indicated at 82 in FIG. 7. That optical signal is directed by optics 83 onto a detector 85, whose electrical signal output is applied to processing circuitry 87 for determining the pressure at the sensor 11.

A second signal, for comparison purposes, is also provided to the processing circuits 87, the second signal coming from a detector 89. The detector 89 is positioned to receive stray light 91 that is reflected from the beam splitter 65 from the source 35. This stray light is of considerable intensity level since the beam splitter 65 is chosen to reflect about half of the light incident upon it.

The pressure related signal from the detector 85 is compared to that from the detector 89, by ratioing or otherwise, within the processing circuits 87 in order to eliminate the effect that variations in the intensity of the source 35 might have on the reflected light 81 which is being measured as an indication of the pressure at the sensor 11. Obviously, it is desired that variations in the intensity of the light source 37 not be erroneously considered to be an indication of changes in pressure being detected by the sensor. Additionally, it may be desirable to eliminate from the reflected optical signal 81 the effect that bending of the fiber 13 might have on the signal in certain circumstances, depending upon the level of accuracy that is desired. The effect of fiber bending can be determined by including adjacent to, and attached to bend with, the fiber 13 another fiber that is not connected to the sensor 11. Variations in transmission of green light from the source 35 in this second fiber are then used to adjust, in the processing circuits 87, the pressure reading being made.

The measurement of temperature by the processing circuit 79 is preferably the same as that described in aforementioned U.S. Pat. No. 4,652,143, the disclosure of which is incorporated herein by reference. Circuits 43 initiate the light source 40 to emit a pulse of light and then cause the processing circuit 79 to monitor decaying luminescent intensity detected by the detector 77 that immediately follows the termination of that excitation pulse. It is the time constant of the decay of the luminescent intensity in this time period that is measured as proportional to temperature.

The measurement of temperature with the sensor 11 being maintained at the temperature of the surrounding material or fluid will, of course, give the temperature of the surroundings. When a measurement of local heat or fluid flow is desired, the sensor 11 is heated by the timing circuits 43 first causing an infrared pulse to be emitted by the source 51. An explanation of how such a technique operates to determine flow is given in aforementioned U.S. Pat. No. 4,621,929, the disclosure of which is hereby incorporated by reference.

Therefore, the processing circuits 79 generate output signals providing an indication of temperature and flow, which are then applied to a display 95 or some other desired read-out device. Similarly, the pressure reading from the processing circuits 87 is so applied to the display 95.

Referring to FIG. 3, a modification of the sensor 11 is shown, with corresponding elements needing no further explanation being indicated by the same reference numbers as used by FIG. 1 but with a prime (') being added. The main difference is the elimination of a separate reflective coating 25. The luminescent particles in the layer 97 are chosen to be of a light color so that they are good reflectors of visible light. Thus, the same three parameters may be measured by a sensor with two layers, using the same optical system as described with respect to FIGS. 6 and 7.

A simplification in the optics and electronics can further be employed, in cases where the luminescent excitation light source 40 is stable enough, by using reflected excitation light for measuring pressure and thus being able to eliminate the separate light source 35. In that case, a beam splitter is positioned in the path of the excitation light before it strikes the dichroic mirror 59 in order to redirect the reflected excitation light onto the detector 85. The use of the detector 89 for monitoring the light source intensity, for use by the processing circuits 87, would also be retained.

The sensors of FIGS. 1 and 3 are not appropriate for measuring the temperature of liquid in which they are immersed since the compressible optical element 21 will have equal pressure on all sides. Therefore, in embodiments of FIGS. 4 and 5, either of the sensors of FIGS. 1 or 3 is provided with an additional element to form a sealed volume immediately around the sensor so that liquid will cause the element 21 to be compressed.

In FIG. 4, a cylindrical sleeve 99 is attached and sealed to the fiber 13. A flexible diaphragm 101 is attached across an end opening of the sleeve 99 in order to seal within the sleeve a space 103. A stiffening disk 105 is preferably attached to the diaphragm 101 in order to easily transfer pressure differentials between a surrounding liquid medium and the fluid within the entrapped chamber 103 to a compressive force applied to the elastomeric optical element 21.

In FIG. 5, an alternative embodiment accomplishes the same purpose. A cylindrical sleeve 107, which may be a capillary tube, is attached and sealed to the optical fiber 13. A sliding, piston-like element 109 is positioned in the open end of the sleeve 107 and is sealed to it by a liquid seal, such as oil, which allows it to move back and forth along the sleeve 107 in response to changes in relative pressure external to the sensor and within a chamber 111.

Although various aspects of the present invention have been explained with respect to specific examples thereof, it will be understood the invention is entitled to protection within the full scope of the appended claims.

It is claimed:
1. A measuring system, comprising:
 a length of an optical fiber transmission medium having first and second ends, said medium consisting of a single optical fiber,
 a sensor attached to said first end of said medium, said sensor including a quantity of substantially optically transparent elastomeric material having a convexly shaped surface extending away from said first medium end and characterized by changing its curvature in response to being compressed by force directed against it, and a flexible layer of optically reflecting material attached to at least a portion of said convex surface in a position that is in optical communication with said medium through its said one end, wherein the reflective material is generally circular in shape and positioned substantially symmetically about a longitudinal axis of said single optical fiber in a manner to occupy only a portion of the field of view of said fiber through its said second end, and wherein a quantity of material characterized by changing a detectable optical characteristic in response to a changing parameter other than displacement, force or pressure is positioned as part of said sensor in another non-overlapping portion of said fiber field of view,
 means provided at said second end of said medium for transmitting optical radiation along the length of said medium against said reflective layer, whereby at least some of said optical radiation is reflected by said layer back along said medium to its said second end, and
 means provided at said second end of said medium for detecting a level of said reflected radiation, thereby measuring a displacement of said reflective layer, whereby the force or pressure applied to said sensor may be determined.

2. The system according to claim 1 wherein said detecting means additionally comprises:
   means provided at said second end of said medium for detecting the level of optical radiation from said radiation transmitting means that enters said medium at said second end, and
   means provided at said second end of said medium for comparing the level of said reflected radiation with the level of radiation being transmitted along said medium.

3. The system according to claim 1 wherein said changing parameter is temperature.

4. The system according to claim 3 wherein said quantity of material includes a luminescent material.

5. The system according to claim 1 which additionally comprises means connected to said reflected radiation detecting means for measuring the pressure against said sensor.

6. The system according to claim 1 wherein said sensor additionally includes means forming a sealed volume around said elastomeric and reflective materials for causing said elastomeric material to be compressed an amount proportional to a differential pressure between that of said volume and that of its surroundings.

7. A measuring system, comprising:
   a length of an optical fiber transmission medium having first and second ends,
   a sensor carried by said first end of said medium, said sensor including a quantity of substantially optically transparent elastomeric material having a non-planar surface extending away from said first medium end and characterized by changing its curvature in response to being compressed by force directed against it and a flexible layer of optically reflective material attached to said non-planar surface in a position that occupies only a portion of the field of view of said medium through its said first end,
   a quantity of material characterized by changing a detectable optical characteristic in response to a changing parameter other than displacement, force or pressure positioned as part of said sensor in another non-overlapping portion of said field of view,
   means provided at said second end of said medium for transmitting optical radiation along the length of said medium against said reflective layer, whereby at least some of said optical radiation is reflected by said layer back along said medium to its said second end,
   means provided at said second end of said medium for detecting a level of said reflected radiation, thereby measuring a displacement of said reflective layer, whereby the force or pressure applied to said sensor may be determined, and
   means provided at said second end of said medium for detecting said optical characteristic simultaneously with detecting said displacement.

8. The system according to claim 7 wherein said parameter is temperature.

9. The system according to claim 8 wherein said quantity of material is further characterized by being substantially transparent to radiation in the infrared range, which additionally comprises a layer of infrared radiation absorbing material carried by said quantity of material on a side thereof removed from said elastomeric material, and further wherein said system additionally comprises means provided at said second end of said medium for directing infrared radiation to said sensor along said medium.

10. The system according to claim 7 wherein said optical radiation transmitting means includes means for restricting said radiation to a first wavelength range, and further wherein said optical characteristic detecting means includes means communicating with said other parameter quantity of material over said medium in a wavelength range substantially non-overlapping with said first wavelength range.

11. The system according to claim 7 wherein said quantity of material includes a luminescent material.

12. The system according to claim 7 wherein the non-planar surface of said quantity of elastomeric material of said sensor includes a convex shape, and wherein said elastomeric material is solid and attached to said first end of said medium.

13. The system according to claim 7 wherein said optical fiber transmission medium consists of a single optical fiber.

14. A measuring system, comprising:
   a length of an optical fiber transmission medium having first and second ends,
   a sensor carried by said first end of said medium, said sensor including a quantity of substantially optically transparent elastomeric material having a non-planar surface extending away from said first medium end and characterized by changing its curvature in response to being compressed by force directed against it, and a flexible layer of optically reflecting material attached to at least a portion of said non-planar surface in a position that is in optical communication with said medium through its said first end, said sensor reflective material including luminescent material characterized by emitting temperature proportional radiation in a first wavelength range when excited by radiation in a second substantially non-overlapping wavelength range,
   means provided at said second end of said medium for transmitting optical radiation within a third wavelength range along the length of said medium against said reflective layer, whereby at least some of said optical radiation is reflected by said layer back along said medium to its said second end, said third wavelength range substantially non-overlapping said first and second wavelength ranges,
   means provided at said second end of said medium for transmitting along said medium to said sensor radiation within said second wavelength range but not said first wavelength range, thereby causing temperature dependent radiation within said first wavelength range to be transmitted back to said second end from said luminescent material,
   means provided at said second end of said medium for detecting a level of said reflected radiation in the third wavelength range, thereby measuring a displacement of said reflective layer, whereby the displacement of the reflecting layer or the force or pressure applied to said sensor may be determined, and
   means provided at said second end of said medium for detecting a level of said luminescent material emitted radiation in the first wavelength range, whereby temperature may be measured by said sensor simultaneously with a measurement of force or pressure.

15. The system according to claim 14 wherein said optical fiber transmission medium consists of a single optical fiber.

16. The system according to claim 14 wherein said reflected radiation detecting means additionally comprises:
- means provided at said second end of said medium for detecting the level of optical radiation within the third wavelength range from said radiation transmitting means that enters said medium at said second end, and
- means provided at said second end of said medium for comparing the level of said reflected radiation within the third wavelength range with the level of radiation being transmitted along said medium within the third wavelength range.

17. The system according to claim 14 wherein the non-planar surface of said quantity of elastomeric material of said sensor includes a convex shape, and wherein said elastomeric material is solid and attached to said first end of said medium.

18. The system according to claim 14 wherein said luminescent material is further characterized by being substantially transparent to radiation in the infrared range, which additionally comprises a layer of infrared radiation absorbing material positioned in thermal contact with the luminescent material on a side thereof that is removed from said elastomeric material, and further wherein said system additionally comprises means provided at said second end of said medium for directing infrared radiation to said sensor along said medium.

19. A system for optically measuring at least first and second parameters, comprising:
- a length of an optical fiber transmission medium having first and second ends,
- a sensor carried by said first end of said medium, said sensor including:
  - a quantity of a solid, substantially optically transparent elastomeric material having a convex surface extending away from said first medium end and characterized by changing its curvature in response to being compressed an amount proportional to force directed against it,
  - a flexible layer of optical radiation reflective material attached to a first portion of said convex surface that is in optical communication with said medium through its said first end, whereby the shape of said layer provides an indication of said first parameter, thereby leaving a second portion of said convex surface in optical communication with said medium through its said first end surrounding said reflective material, and
  - means positioned on at least some of said second convex surface portion for providing an optical indication of said second parameter,
- means provided at said second end of said medium for transmitting optical radiation along the length of said medium to said reflective layer, whereby an amount of said optical radiation proportional to said first parameter is reflected by said layer back along said medium to its said second end,
- means provided at said second end of said medium for detecting a level of said reflected radiation, thereby providing an optical signal proportional to said first parameter, and
- means provided at said second end of said medium for optically communicating with said second parameter optical indication means in a manner to provide an optical signal proportional to said second parameter.

20. The system according to claim 19 wherein said second parameter is temperature, said sensor includes means positioned in thermal communication with said second parameter optical indication means for absorbing infrared radiation, and additionally comprising means provided at said second end of said medium for transmitting infrared radiation along said medium to said sensor, thereby being absorbed by said infrared radiation absorbing means, whereby the measurement of said temperature is proportional to a third parameter.

21. The system according to claim 20 wherein said optical radiation transmitting means is characterized by transmitting said optical radiation within a first defined wavelength range, and said second parameter optical communication means is characterized by communicating over said optical fiber medium with said second parameter optical indication means within a second wavelength range that does not overlap said first defined wavelength range, neither of said first or second wavelength ranges overlapping with that of said infrared radiation.

22. The system according to claim 19 wherein said optical radiation transmitting means is characterized by transmitting said optical radiation within a first defined wavelength range, and said second parameter optical communication means is characterized by communicating over said optical fiber medium with said second parameter optical indication means within a second wavelength range that does not overlap said first defined wavelength range.

23. A sensor carried by an end of at least one optical fiber, said sensor comprising:
- a quantity of substantially optically transparent elastomeric material having a non-planar surface extending away from said one medium end and characterized by changing its curvature in response to being compressed by force directed against it, and
- a flexible layer of optical radiation reflective material attached to at least a portion of said non-planar surface in a position that is in optical communication with said medium through its said one end, whereby an optically detectable shape of the reflective material changes as a force is applied to said sensor,
- wherein the reflective material layer includes a solid area positioned to occupy only a portion of the field of view of said optical fiber through its said end, and wherein a quantity of material characterized by exhibiting a detectable optical change as a function of temperature is positioned as part of said sensor in another non-overlapping portion of said field of view.

24. The system according to claim 23 wherein said sensor additionally comprises a layer of infrared radiation absorbing material positioned in thermal contact with said temperature detecting material.

25. The sensor according to claim 23 wherein said sensor is carried by an end of only one optical fiber.

26. A three parameter sensor carried by an end of a single optical fiber having a central longitudinal axis, said sensor comprising:
- a substantially transparent elastomeric optical element attached to said fiber end and having a convex shaped surface extending away from said fiber end but being in optical communication therewith, a continuous flexible layer of optical radiation reflective material attached to a portion of said surface, whereby an optically detectable shape of the reflective material changes as a force is applied to compress said elastomeric element, thereby to sense a first parameter, a layer of material characterized by exhibiting a detectable optical change as a function of temperature attached to at least a portion of said surface adjacent said reflective material, thereby to sense a second parameter, and a layer of infrared radiation absorbing material positioned over at least said temperature detecting material layer and in thermal contact therewith, thereby allowing determination of a third parameter.

27. A measuring system, comprising:

a length of an optical fiber transmission medium having first and second ends, said medium consisting of a single optical fiber, a sensor attached to said first end of said medium, said sensor including a quantity of substantially optically transparent elastomeric material having a convexly shaped surface extending away from said first medium end and characterized by changing its curvature in response to being compressed by force directed against it, and a flexible layer of optically reflecting material attached to at least a portion of said convex surface in a position that is in optical communication with said medium through its said one end, said optically reflective material including luminescent material characterized by changing at least one detectable optical characteristic in proportion to its temperature means provided at said second end of said medium for transmitting optical radiation along the length of said medium against said reflective layer, whereby at least some of said optical radiation is reflected by said layer back along said medium to its said second end, and means provided at said second end of said medium for detecting a level of said reflected radiation, thereby measuring a displacement of said reflective layer, whereby the force or pressure applied to said sensor may be determined.

28. A sensor, comprising:

a length of a single optical fiber, a solid quantity of substantially optically transparent elastomeric material attached to one end of said optical fiber length and having a convex surface extending away from said one fiber end and characterized by changing its curvature in response to being compressed by force directed against it, and a flexible layer of optical radiation reflective material attached to at least a portion of said convex surface in a position that is in optical communication with said optical fiber through its said one end, whereby an optically detectable shape of the reflective material changes as a force is applied to said sensor, said optically reflective material including luminescent material characterized by changing at least one detectable optical characteristic in proportion to its temperature.

29. The system according to claim 28 wherein said sensor additionally comprises means forming a sealed volume around said elastomeric and reflective materials for causing said elastomeric materials to be compressed by an amount proportional to a differential pressure between that of said volume and that of its surroundings.

30. A multi-parameter sensor, comprising:

a length of a single optical fiber having first and second ends, a flexible layer of optical radiation reflective material, a resilient element holding said reflective layer in optical communication with the first fiber end in a manner that said reflective layer is normally in a curved shape while allowing the reflective layer to flatten an amount proportional to the amount of force applied to the resilient element, thereby to affect the degree of optical coupling between the reflective layer and said fiber, whereby a determination of a first parameter related to the amount of such force may be made from the amount of light reflected from the reflective layer to the second fiber end, and a quantity of material characterized by exhibiting a detectable optical change as a function of temperature positioned in optical communication with said fiber through said first end, thereby allowing a determination from the second fiber end of sensor temperature as a second parameter.

31. The multi-parameter sensor according to claim 30 which additionally comprises a layer of infrared radiation absorbing material positioned over at least said temperature detecting material and in thermal contact therewith, thereby allowing determination of a third parameter.

32. The combination of claim 31 wherein said sensor is made part of a catheter structure.

33. The combination of claim 30 wherein said sensor is made part of a catheter structure.

34. A multi-parameter measuring system, comprising:

a length of an optical fiber transmission medium having first and second ends, a multi-parameter sensor attached to said medium first end, said sensor including:

resilient means carrying a layer of flexible optically reflecting material for controlling the degree of curvature thereof in response to an external force being applied to the sensor, thereby to cause a degree of optical coupling between the reflecting layer and said medium to be controlled as an indication of a first parameter, and a quantity of luminescent material positioned in optical communication with said medium, said luminescent material being characterized by emitting, when excited by optical radiation in a first wavelength range, optical radiation in a second wavelength range that has a detectable characteristic that is dependent upon temperature of the luminescent material, said first and second optical wavelength ranges being substantially non-overlapping, means provided at said second medium end for transmitting optical radiation within a third wavelength range along the length of said medium against said reflective layer, whereby an amount of said optical radiation proportional to the curvature of the reflective layer is reflected back along said medium to its said second end, said third optical wavelength range being substantially non-overlapping with said first and second wavelength ranges, means provided at said second medium end for measuring a level of said reflected radiation, thereby measuring a quantity proportional to the curvature of said reflective layer, whereby said first parameter may be determined, means provided at said second medium end for transmitting optical radiation within said first wavelength range along the length of said medium against said luminescent material, whereby optical radiation within the second wavelength range is emitted back along said medium to its said second end, and means provided at said second medium end for measuring the temperature dependent detectable characteristic of said second wavelength range emitted radiation, whereby the temperature of the sensor may be determined as a second parameter.

35. The measuring system according to claim 34 wherein said sensor additionally includes a layer of infrared radiation absorbing material positioned in thermal contact with said luminescent material, and wherein the system additionally comprises means provided at said second medium end for transmitting infrared radiation along said fiber medium to said infrared radiation absorbing material, thereby allowing determination of a third parameter.

36. The measuring system of claim 35 wherein said sensor is attached to a single optical fiber.

37. The measuring system according to claim 34 wherein said sensor is attached to a single optical fiber.

38. The measuring system according to claim 34 wherein the reflective layer and luminescent material of the sensor are positioned in adjacent non-overlapping positions.

39. The measuring system according to claim 34 wherein the reflective layer and luminescent material of the sensor are combined into a single layer.

40. A system for measuring displacement, force or pressure, comprising:

a length of an optical fiber transmission medium having first and second ends, a sensor attached to said medium first end, said sensor including resilient means carrying a layer of flexible optically reflecting material for controlling the degree of curvature thereof in response to an amount of displacement that results from an external force being applied to the sensor, thereby to cause a degree of optical coupling between the reflecting layer and said medium to be dependent upon the amount of such displacement, said sensor additionally including a means responsive to interrogating optical radiation for providing an optical signal proportional to temperature, and wherein the system additionally comprises means provided at said second medium end for detecting said temperature proportional optical signal and providing a measure of the temperature of the sensor, means provided at said second medium end for transmitting optical radiation along the length of said medium against said reflective layer, whereby an amount of said optical radiation proportional to the amount of displacement of the reflective layer is reflected back along said medium to its said second end, means provided at said second medium end for measuring a level of said reflected radiation, thereby measuring a quantity proportional to the amount of displacement of said reflective layer, and means responsive to the level of reflected radiation for determining any of the displacement of the reflective layer or force pressure applied to said sensor.

41. The system according to claim 40 wherein sensor is attached to a single optical fiber.

42. The system according to claim 40 wherein the resilient element of said sensor includes a quantity of substantially optically clear elastomeric material.

43. A method of measuring at least temperature and pressure within a human body, comprising the steps of:

implanting within said body a sensor and a length of optical fiber to which the sensor is attached at one end, said sensor including:

resilient means carrying a layer of flexible optically reflecting material for controlling the degree of curvature thereof in response to external pressure, thereby to cause a degree of optical coupling between the reflecting layer and said fiber to be dependent upon the amount of such pressure, and a quantity of luminescent material positioned in optical communication with said medium, said luminescent material being characterized by emitting, when excited by optical radiation in a first wavelength range, optical radiation in a second wavelength range that has a detectable characteristic that is dependent upon temperature of the material, said first and second optical wavelength ranges being substantially non-overlapping, directing along the optical from outside of the body optical radiation within a third wavelength range that is substantially non-overlapping with said first and second wavelength ranges, wherein at least a portion of said third wavelength range radiation is reflected back along the optical fiber from the reflecting material layer of the sensor, directing along the optical fiber from outside of the body optical radiation within said first wavelength range, wherein optical radiation in the second wavelength range is emitted back along the optical fiber, and detecting the optical radiation within the second and third wavelength ranges, thereby to determine quantities that are proportional to the temperature and pressure, respectively, within the body at the location of the sensor.

44. A method according to claim 43 wherein the step of implanting the sensor and optical fiber includes implanting a single optical fiber as part of a catheter.

* * * * *

UNITED STATES PATENT AND TRADEMARK OFFICE
CERTIFICATE OF CORRECTION

PATENT NO. : 4,986,671

DATED : January 22, 1991

INVENTOR(S) : Mei H. Sun and Kenneth A. Wickersheim

It is certified that error appears in the above-identified patent and that said Letters Patent is hereby corrected as shown below:

Column 13, line 67, in Claim 29:  replace "materials" with --material--

Column 16, line 9, in Claim 40:  insert --or-- after "force"

Column 16, line 39, in Claim 43:  insert --fiber-- after "optical"

Signed and Sealed this

Twenty-eighth Day of July, 1992

Attest:

DOUGLAS B. COMER

*Attesting Officer*   *Acting Commissioner of Patents and Trademarks*